United States Patent [19]

Zinreich et al.

[11] Patent Number: 5,368,030
[45] Date of Patent: Nov. 29, 1994

[54] NON-INVASIVE MULTI-MODALITY RADIOGRAPHIC SURFACE MARKERS

[75] Inventors: Simion J. Zinreich; Eva S. Zinreich, both of Owings Mills, Md.; David C. Howson, Denver, Colo.

[73] Assignee: Izi Corporation, Owings Mills, Md.

[21] Appl. No.: 942,715

[22] Filed: Sep. 9, 1992

[51] Int. Cl.⁵ .......................... A61B 6/00; A61B 5/055
[52] U.S. Cl. ................. 128/653.1; 128/653.2; 324/309; 378/163
[58] Field of Search ............ 128/653.1, 653.2, 653.5, 128/639, 640, 641; 250/370.1; 378/162–165; 356/247–248; 156/145, 146, 242; 264/250, 259; 324/308, 309

[56] References Cited

U.S. PATENT DOCUMENTS

| | | | |
|---|---|---|---|
| 3,977,392 | 8/1976 | Manley | 128/641 |
| 4,617,935 | 10/1986 | Cartmell et al. | 128/641 |
| 4,710,875 | 12/1987 | Nakajima et al. | 378/162 |
| 4,774,957 | 10/1988 | Nambu et al. | 128/653.5 |
| 5,071,602 | 12/1991 | Nambu et al. | 128/653.5 |
| 5,193,106 | 3/1993 | DeSena | 378/163 |

FOREIGN PATENT DOCUMENTS 1088706  4/1985  U.S.S.R. ............. 128/653.1

*Primary Examiner*—K. M. Pfaffle
*Attorney, Agent, or Firm*—Lyon & Lyon

[57] ABSTRACT

The device of the present application, an adhesive disk, relates to non-invasive multi-modality radiographic surface markers and provides means for marking patients and diagnostic images taken of those patients through different methods including X-Ray, Computerized Tomography, Positron Emission Tomograph, and Nuclear Magnetic Resonance Imaging among others. The device of the present application also provides means for enabling the accurate location of internal structures of a patient.

3 Claims, 1 Drawing Sheet

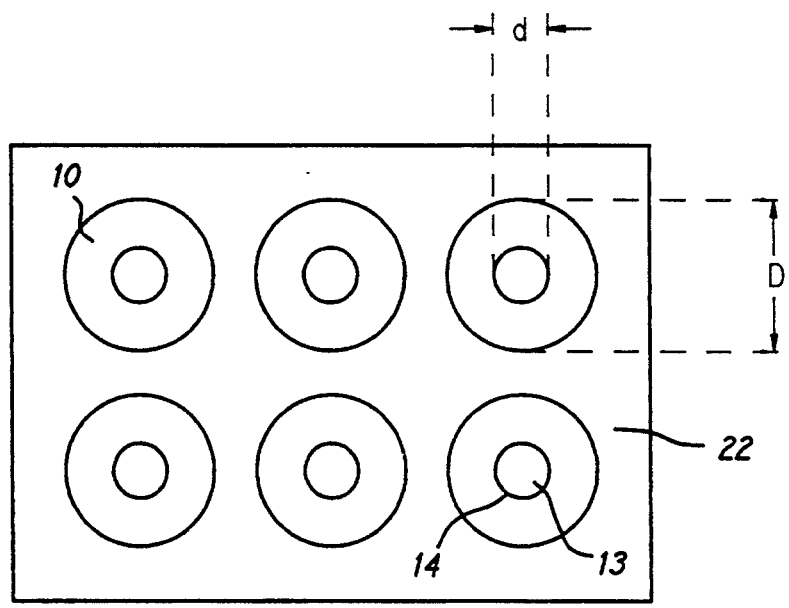
Fig. 1.
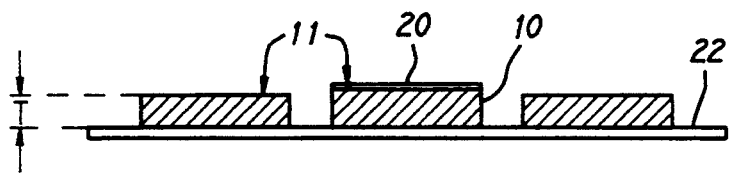
Fig. 2.
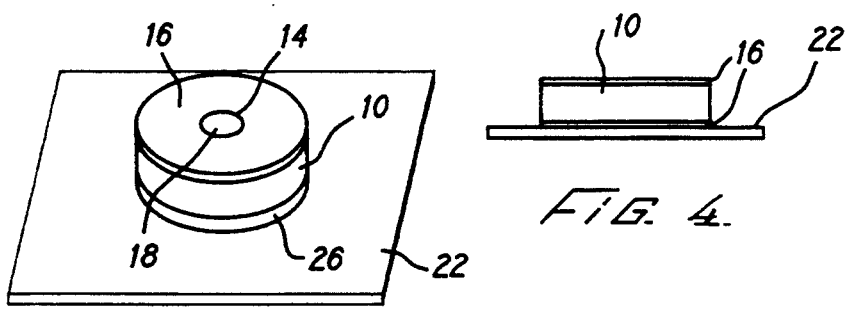
Fig. 3.
Fig. 4.
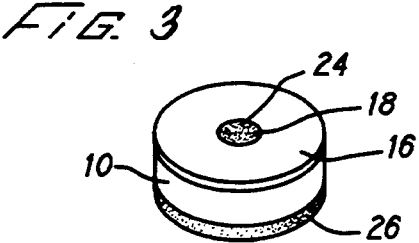
Fig. 5.
Fig. 6.
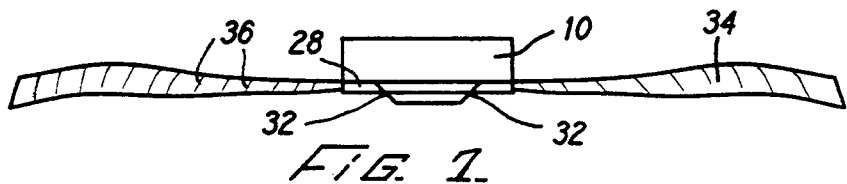
Fig. 7.

NON-INVASIVE MULTI-MODALITY RADIOGRAPHIC SURFACE MARKERS

FIELD OF THE INVENTION

The device of the present application relates to radiographic surface markers, particularly non-invasive radiographic surface markers useful in multiple diagnostic techniques.

BACKGROUND

Radiologists and others use a number of methods to create images of structures within a patient's body to help diagnose diseases and guide therapeutic procedures. Methods used include, for example, conventional X-Ray, Computerized Tomography ("CT"), ultrasound, Positron Emission Tomography ("PET"), and (Nuclear) Magnetic Resonance Imaging ("NMR" or "MRI"), among others. These methods respectively employ X-radiation (both the X-Ray and CT methods), sound, radio active emissions, and magnetic fields in combination with radio-frequency electromagnetic radiation, to create images of structures within the patient's body.

When creating such diagnostic images of a patient, it is desirable to use surface anatomical features which are visible both on the patient and on the diagnostic image of that patient as reference points to facilitate the performance of surgical or other therapeutic intervention techniques. Reference points defined on both a patient's body and a diagnostic image of interior features of that patient's body, allow a physician to geometrically calculate the precise location of a particular site within the patient's body or a particular position of a specific structure within the patient's body. Pin-pointing the location of a particular site or structure allows the physician to more easily and accurately biopsy or otherwise treat the area.

However, there often are no surface anatomical features on the patient's body adequate to use as such reference points (e.g. such features may not exist or may not be located appropriately for such use). If there are no anatomical reference points on the surface of the patient's body, one is unable to precisely locate a target site or structure shown in a two dimensional diagnostic image. The location of the target site or structure is obscure because the two-dimensional diagnostic image does not provide sufficient information for a geometric relationship between a surface point on the patient's body and the target site or structure to be accurately calculated (i.e. it is unclear at what point on the patient's body the diagnostic image scan was taken).

In such cases, it is desirable to place artificial reference markers on the patient's skin to serve as reference points. A physician may place artificial markers in positions which are optimal reference points relative to the location of target tissues within the patient's body. The markers are designed to clearly show unique and identifiable reference points on both the surface of the patient's body and on the diagnostic image.

Furthermore, it is becoming increasingly important to align images formed by different imaging methods to better identify pathologic structures. Aligning, or "rectifying," images and other radiographic data formed by different imaging methods would be substantially improved (in both ease and accuracy) through the use of surface markers which create reference points visible to a multiplicity of imaging methods. Such surface markers would facilitate the precise super-imposition of imaging data from CT, MRI, and other sources for optimal correlation of tissues and physiologic processes which are demonstrated using these various methods.

Surface markers of various shapes and sizes are generally shown in the prior art. However, such prior art surface markers are inadequate to address the problems described above. There is no surface marker disclosed which is satisfactorily visible to a variety of imaging methods. For example, one commercial product today uses a small, dense metal bead attached to adhesive tape. The metal is dense to X-radiation and the adhesive allows rapid, secure attachment to the patient's skin. However, the metal produces an imaging artifact at certain useful X-radiation intensities and it is transparent to methods such as MRI. Moreover, with MRI a aberration is produced which obscures adjacent tissue, rendering the image useless. Therefore, this surface marker is not satisfactory.

It would be useful to have a material which is dense to all of the commonly used imaging methods and which does not produce aberrations that obscure portions of the image.

SUMMARY OF THE INVENTION

The invention of the present application comprises multiple modality surface markers which are appropriate to use as artificial reference points and which are visible both on a patient and on diagnostic images taken by various methods. The multi-modality surface markers of the present invention are visible to many imaging methods. In addition, they do not produce undesirable images which obscure portions of desirable images.

Accordingly, it is a principal object of the present invention to provide surface markers for use as reference points on diagnostic images and which are dense to multiple imaging methods such as X-Ray, CT, ultrasound, PET, MRI, and others.

It is a further object of the present invention to provide surface markers for use as reference points on diagnostic images and which do not produce undesirable aberrations which obscure portions of the diagnostic images.

It is also an object of the present invention to provide multi-modality surface markers which adhere to a patient's skin over a period of time sufficient to permit a variety of imaging methods performed while the markers remain in place.

It is an additional object of the present invention to provide multi-modality surface markers which are inexpensive and, therefore, are economical to use even when using several markers at one time.

It is another object of the present invention to provide multi-modality surface markers which may be repositioned if necessary.

It is yet another object of the present invention to provide multi-modality surface markers which are shaped to maximize their utility in most common and important imaging applications.

The present invention relates to novel surface markers which are dense to a multiplicity of imaging methods, are suitable for use as reference points on diagnostic images, and do not result in obscuring portions of the diagnostic images in which they are used. The surface markers of the present invention adhere to a patient's skin sufficient to allow several procedures to be performed without the markers accidentally moving. In addition, the markers of the present invention are inexpensive and may be repositioned, and, therefore, economically allow using multiple markers in a single procedure and allow moving the makers to a most desired location. Furthermore, the markers of the present invention are shaped to maximize their utility in most common imaging applications.

BRIEF DESCRIPTION OF THE DRAWINGS

FIG. 1 shows a plan view of a set of six surface markers of the present invention.

FIG. 2 shows a side view of the set of surface markers of FIG. 1.

FIG. 3 shows a perspective view of an additional embodiment of a surface marker of the present invention.

FIG. 4 shows a side view of the surface marker of FIG. 3.

FIG. 5 shows a perspective view of another embodiment of a surface marker of the present invention.

FIG. 6 shows a plan view of a plastic disk.

FIG. 7 shows a side view of an embodiment of a surface marker and tape of the present invention.

DETAILED DESCRIPTION OF THE PREFERRED EMBODIMENT

The multi-modality surface markers 10 of the present invention comprise a disk-like marker 10 made from a material which has a mobile phase suitable for MRI imaging by commercial machines and which is sufficiently X-Ray-opaque for adequate imaging on CT or X-Ray.

A wide variety of materials and designs have been tested to discover materials which have adequate imaging qualities under multiple imaging methods and which can be manufactured at low cost. Both combinations of materials and individual materials have been tested.

Imaging with X-radiation (X-rays and CT scans) requires that a reference marker 10 comprise a material which impedes the transmission of radiation at the wavelength used in commercial machines. Metals and materials which contain metal salts are popular for these techniques. However, certain organic materials, and other non-metallic materials also have adequate opacity.

A reference marker 10 for use with MRI depends on entirely different properties. With this modality, a powerful magnetic field is applied which orients the rotational axis of atomic nuclei along a single vector. Upon removal of the magnetic field, the spinning nuclei revert to a random distribution of axial orientation- In the process of reverting the nuclei emit radiation at characteristic frequencies. By detecting this radiation a computer, using mathematical formulae, can compose an image based on the different intensities from different tissues.

Reference markers 10 for use with MRI require mobile atomic nuclei in a liquid state. Commercial MRI machines also detect frequencies and intensities of radiation typically emitted from aqueous solutions or composites. Certain organic compounds also emit frequencies detectable by commercial machines.

The preferred embodiment of the reference marker 10 of the present invention uses a material which has a mobile phase suitable for MRI imaging by commercial machines and which is sufficiently opaque to X-radiation that it is adequate for imaging on CT or X-Ray. The preferred embodiment uses a gel which is commercially available and is manufactured by Promeon, Inc. However, other commercially-produced materials can be used and other materials could be developed which would also work well.

As shown in FIGS. 1 and 2, the marker 10 of the present invention comprises a circular disk 12 approximately fifteen millimeters in outer diameter D and two and one-half millimeters thick T made from a gel material. The marker 10 has a center 13 comprising a central axial hole 14 of approximately four millimeters in diameter d. The gel material is available in sheet form. The material is die-cut and several layers are laminated together to form the present marker 10. Other useful shapes may be formed and assembled out of the gel material.

As shown in FIGS. 3 and 4, when the marker 10 is to be used with PET scans the central axial hole 14 is enclosed by membrane 16 on the top and a plastic disk 26 on the bottom to form a sealed central Well 18 (FIG. 3) capable of containing liquid. A liquid imaging agent may be injected, using a conventional hypodermic needle, into the sealed well 18 through the top membrane 16 thereby making the marker 10 visible to PET scans.

Multiple markers 10 may be economically laminated and die-cut by methods well known in the art. The marker 10 preferably comprises multiple layers of Promeon gel laminated together to achieve the required thickness and mechanical strength. As shown in FIG. 2, the preferred embodiment includes a plastic film 20 laminated on a top surface 11 of the marker 10 to reinforce the shape of the marker 10 and to reduce water loss from the marker 10 by evaporation. Reduction of water loss is important because water loss reduces the marker's density to certain radiographic modalities (e.g. MRI). The marker 10 may be further laminated onto a plastic film backing 22 allowing for the marker to be easily peeled-off and may be stored in a sealed envelope to further reduce evaporation.

A user typically will obtain a package which contains multiple markers 10 on a single film backing 22. To use the markers 10, the user will open a sealed envelope containing the markers 10 and take out the film backing 22 which carries the markers 10. The user will then remove a marker 10 from the backing 22 and apply it to the desired location on a patient's skin. One or more markers 10 may be so applied depending on the procedures to be used and the reference points desired.

In images created from either MRI or X-Ray modalities (including CT) a marker 10 appears in side view as a heavy, bright line on a negative image or a heavy, dark line on a position image. If the image is taken perpendicular to a top surface 11 of the marker 10, the marker 10 appears as a bright disk shape on negative images or as a dark disk shape on positive images.

With scanned images, such as CT or MRI, the plane of the scan would typically pass through a marker 10 parallel to the surface of the marker surface 11 thereby slicing through the marker 10. Therefore, scanned images generally show the marker 10 in cross-section normal to the marker surface 11.

A first scan that intersects the marker 10 shows on an image as a very short line or dot because the scan intersects the marker 10 through a short section. A second scan shows on an image as a longer line because a longer section of the marker 10 is intersected by the scan. As the scans begin to intersect the marker 10 near the marker's center 13, the image of the marker 10 shows a gap due to the scan intersecting the central hole 14. A scan through the center 13 of the marker 10 shows the widest gap in the image due to the scan intersecting the marker 10 through the center of the central hole 14 where the hole 14 is the widest. One may measure the size of the gap present in an image and thereby directly visualize the spatial relationship between the center 13 of the marker 10 and any underlying structures or pathology of the patient.

By using multiple markers and multiple scans one may precisely triangulate the location of deep structures of the patient relative to the array of surface markers 10. These relationships may then be used to guide a surgical approach or other medical procedure.

The central hole 14 is designed to permit passage of needles or other instruments for sampling tissues or for surgically ablating tissues. The markers 10 may optionally be sterilized and/or provided by the manufacturer sterile. Sterilization of the markers 10 avoids potential infection of a patient due to an accidental passage of infectious organisms from the surface of the marker 10 and avoids contamination of the sterile field prepared on a patient prior to a biopsy procedure.

The nature of the preferred material readily permits the production of a wide variety of two- and three-dimensional shapes for use in particular procedures. The marker 10 shown and described above represents some commonly useful embodiments. Other embodiments use composites of laminated layers of different materials to achieve the objectives of providing multi-modal imaging, self-adhesion, and useful geometric shapes. For example, an X-Ray-opaque metal ink may be used to print a useful pattern on one layer of a laminated marker structure. Other laminae may include materials and shapes which may be visible through MRI or other modalities.

Liquid materials may also be used to provide optimal visible density on MRI or other imaging modalities. Such liquids can be captured within the hollow pocket 18 or on a porous matrix of a vapor-retarding material 24 included in the hollow pocket of a marker 10. As shown in FIG. 5, in one such embodiment, the center hole 14 of the marker 10 comprises a closed chamber or well 18 which further contains a sponge-like matrix 24. The chamber 18 is closed by a thin polymer film 16 on the top and a rigid plastic disk 26 on the bottom. In one use of this marker 10, a user prepares a nuclide such as those known and used in PET scans. The user then injects a small volume of the nuclide into the sponge-like matrix contained in the closed chamber 18 by penetrating the top film 16 with a hypodermic needle. The top film 16 retains the liquid within the sponge-like matrix and the bottom plastic plate prevents the needle from protruding through the marker 10 into the patient's skin. The patient is then ready to be scanned.

The markers 10 may be used as components in assemblies which enhance a user's ability to locate structures. In one embodiment each marker 10 includes a perforated plastic plate 28 as shown in FIG. 6 on one surface. The plate 28 has a perforation 30 for aligning the plate 28 with the hole 14 in the gel marker 10. The plate 28 also has slots 32 to permit the insertion of a flat tape 34 as shown in FIG. 7. The tape 34, which is not radio opaque, may be printed with linear marks 36 and may accommodate more than one marker 10. The markers 10 and plate slots 32 are designed such that a user can slide the markers 10 independently along the tape 34. This allows the user to measure the distance between markers 10 along the skin surface and even over complex contours. The user may attach the markers 10 to the patient's skin at desired points thereby also attaching the tape 34 to the patient. The markers 10 and tape 34 remain on the patient during and after an imaging procedure. The tape 34 allows instant determination of the distance between markers 10. After developing an image, the user may then use the markers 10 and tape 34 to more accurately locate structures visualized on the image.

The tape 34 may also comprise means for otherwise attaching the tape 34 to a patient. For example, the tape 34 may include hook and loop fastener means (such as commonly known Velcro fasteners) on its ends for allowing the tape 34 to be wrapped around a patient and its ends securely fastened together thereby holding the tape 34 securely on the patient.

While embodiments of the present invention have been shown and described, various modifications may be made without departing from the scope of the present invention, and all such modifications and equivalents are intended to be covered.

What is claimed is:

1. A radiographic surface marker comprising
   a gel material visible to multiple radiographic imaging methods, said gel material comprising multiple layers of said gel material laminated together forming a first surface and a second surface,
   said layers of said gel materials having an aperture therethrough forming first and second openings,
   a membrane on said first surface of said gel material and sealing said first opening,
   a disk on said second surface of said gel material and sealing said second opening to form a chamber, and
   a porous material contained in said chamber.

2. A radiographic surface marker comprising
   a gel material visible to multiple radiographic imaging methods, said gel material comprising multiple layers of said gel material laminated together forming a first surface and a second surface,
   said layers of said gel material having an aperture therethrough,
   a first membrane on said first surface of said gel material,
   a second membrane on said second surface of said gel material and,
   a plate on said second membrane, said plate having a perforation for alignment with said aperture and having slots for attaching said marker to a tape for removably attaching said marker to a patient.

3. The radiographic surface marker of claim 2 further including the tape to which the marker is attached wherein the tape includes printed marks thereon.

* * * * *